US009675570B2

(12) United States Patent
Tajiri et al.

(10) Patent No.: US 9,675,570 B2
(45) Date of Patent: Jun. 13, 2017

(54) SOLID COMPOSITIONS COMPRISING A SALT OF AMINOCARBOXYLIC ACID

(71) Applicant: Daiichi Sankyo Company, Limited, Tokyo (JP)

(72) Inventors: Shinichiro Tajiri, Kanagawa (JP); Masami Takemura, Kanagawa (JP); Shinji Yoshinaga, Kanagawa (JP)

(73) Assignee: DAIICHI SANKY COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/553,341

(22) Filed: Nov. 25, 2014

(65) Prior Publication Data

US 2015/0079166 A1    Mar. 19, 2015

Related U.S. Application Data

(63) Continuation of application No. PCT/JP2014/059812, filed on Apr. 3, 2014.

(30) Foreign Application Priority Data

Apr. 4, 2013 (JP) ................ 2013-079006

(51) Int. Cl.
*A61K 31/195* (2006.01)
*A61K 47/12* (2006.01)
*A61K 9/20* (2006.01)
*A61K 47/38* (2006.01)
*A61K 47/10* (2006.01)
*A61K 47/26* (2006.01)
*A61K 31/197* (2006.01)
*A61K 9/28* (2006.01)

(52) U.S. Cl.
CPC .............. *A61K 31/195* (2013.01); *A61K 9/20* (2013.01); *A61K 9/2853* (2013.01); *A61K 31/197* (2013.01); *A61K 47/10* (2013.01); *A61K 47/12* (2013.01); *A61K 47/26* (2013.01); *A61K 47/38* (2013.01)

(58) Field of Classification Search
None
See application file for complete search history.

(56) References Cited

U.S. PATENT DOCUMENTS

| 6,054,482 | A | 4/2000 | Augart et al. |
| 7,947,738 | B2 | 5/2011 | Shimada et al. |
| 8,895,141 | B2 | 11/2014 | Satomi et al. |
| 2010/0249229 | A1* | 9/2010 | Shimada ............... C07C 229/32 514/530 |
| 2011/0135927 | A1 | 6/2011 | Satomi et al. |
| 2012/0071685 | A1 | 3/2012 | Kitagawa et al. |
| 2012/0156261 | A1* | 6/2012 | Fujiwara .............. A61K 9/0056 424/400 |

FOREIGN PATENT DOCUMENTS

| CS | 101878193 A | 11/2010 |
| JP | 11-189547 A | 7/1999 |
| JP | 2001-064177 A | 3/2001 |
| JP | 2007-131542 A | 5/2007 |
| JP | 4479974 B2 | 3/2010 |
| JP | 2010-241796 A | 10/2010 |
| WO | WO 01/12193 A1 | 2/2001 |
| WO | WO2006/056874 * | 6/2006 |
| WO | WO 2006/056874 A1 | 6/2006 |
| WO | WO 2010/021300 A1 | 2/2010 |

OTHER PUBLICATIONS

Cutrignelli et al., "Comparative effects of some hydrophilic excipients on the rate of gabapentin and baclofen lactamization in lyophilized formulations," *International Journal of Pharmaceutics*, (2007), 332:98-106.
Hashida (Ed.), "The Design and Evaluation of Oral Medications," Published Feb. 10, 1995 by Yakugyo Jiho Co., Tokyo, Japan, pp. 50-51.
Tsuda (Ed.), "Course X, Fundamentals of Pharmaceutical Development," Published Mar. 1, 1971 by Chijin Shoka Co., Ltd., Tokyo, Japan, pp. 161-162, 167, 170-171, and 179.
English translation of International Search Report issued Apr. 28, 2014, in PCT Application No. PCT/JP2014/059812, 2 pages.

* cited by examiner

*Primary Examiner* — Melissa Javier
(74) *Attorney, Agent, or Firm* — Dorsey & Whitney LLP

(57) ABSTRACT

The present disclosure provides solid compositions comprising a stabilized salt of aminocarboxylic acid. Pharmaceutical compositions comprising [(1R,5S,6S)-6-(aminomethyl)-3-ethylbicyclo[3.2.0]hept-3-en-6-yl]acetic acid monobenzenesulfonate in combination with appropriate additives are also provided.

4 Claims, 2 Drawing Sheets

Figure 1 total amount of related substances under 40°C, 75% RH, 6 months(%)
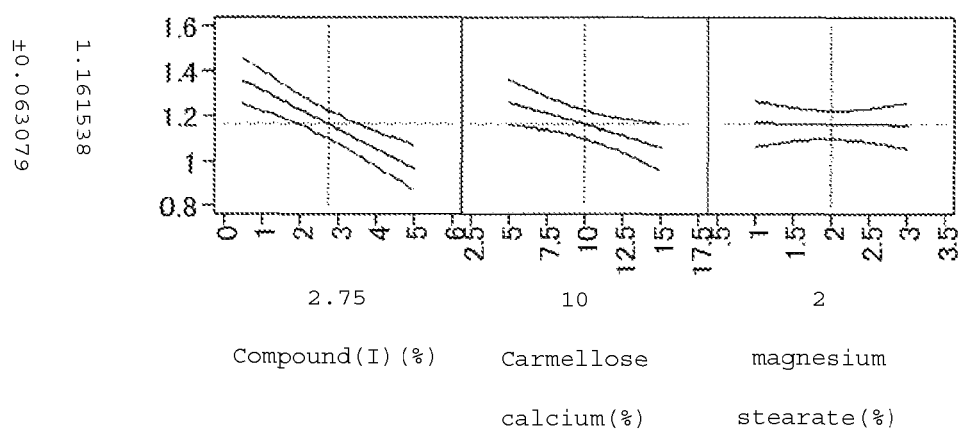
Figure 2
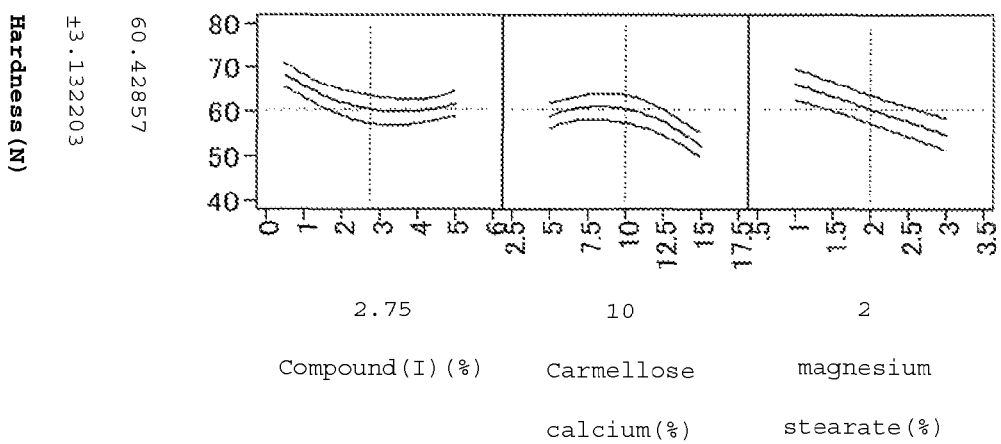

SOLID COMPOSITIONS COMPRISING A SALT OF AMINOCARBOXYLIC ACID

This application claims the benefit under 35 U.S.C. §111 (a) as a continuation application of International Application No. PCT/JP2014/059812, filed Apr. 3, 2014, entitled "Solid Composition Comprising Salt of Aminocarboxylic Acid," which claims priority to Japanese Patent Application No. 2013-079006, filed Apr. 4, 2013.

TECHNICAL FIELD

The present invention relates to stabilized pharmaceutical solid compositions of [(1R,5S,6S)-6-(aminomethyl)-3-ethylbicyclo[3.2.0]hept-3-en-6-yl]acetic acid monobenzenesulfonate (hereinafter, also referred to as "compound (I)"), and methods for preparing the stabilized pharmaceutical solid compositions.

The present invention also relates to solid preparations in the form of stabilized tablets, powders, granules, and capsules comprising compound (I), and methods for producing these solid preparations in the form of stabilized tablets, powders, granules, and capsules.

BACKGROUND ART

Compound (I) represented by the following structural formula:

[Formula 1]

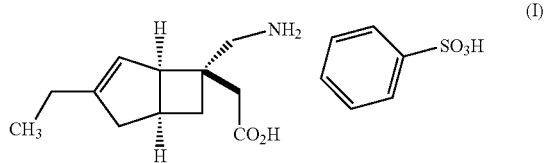

is disclosed in US 2010/249229. This compound (I) has excellent activity as an $\alpha_2\delta$ ligand and as such, is expected to have excellent therapeutic and/or preventive effects on disorders such as pain and central nervous system involvement.

CITATION LIST

Patent Literature

[Patent Literature 1] US 2010/249229

SUMMARY OF INVENTION

Technical Problem

The present inventors have conducted diligent studies on stabilized pharmaceutical solid compositions of compound (I) and methods for preparing stabilized pharmaceutical solid compositions, and further on solid preparations in the form of stabilized tablets, powders, granules, and capsules of compound (I) and methods for producing these solid preparations in the form of stabilized tablets, powders, granules, and capsules. Consequently, the present inventors have solved problems associated therewith and completed the present invention.

Solution to Problem

Specifically, the present invention provides, as described below, stabilized pharmaceutical solid compositions of compound (I) represented by the following structural formula:

[Formula 2]

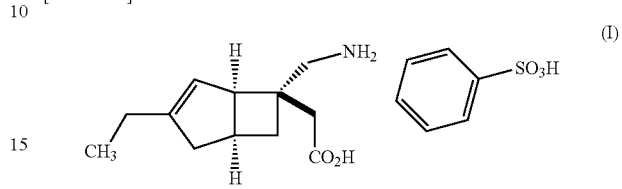

and methods for preparing the stabilized pharmaceutical solid compositions, and further provides solid preparations in the form of stabilized tablets, powders, granules, and capsules of compound (I) and methods for producing these solid preparations in the form of stabilized tablets, powders, granules, and capsules.

Preferred aspects of the present invention are as shown below.

[1] A pharmaceutical solid composition comprising [(1R,5S,6S)-6-(aminomethyl)-3-ethylbicyclo[3.2.0]hept-3-en-6-yl]acetic acid monobenzenesulfonate which is a compound represented by the following formula (I):

[Formula 3]

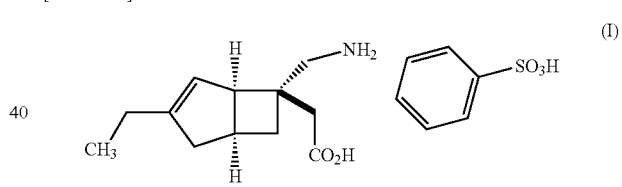

in combination with (i) one or two or more component(s) selected from the group consisting of D-mannitol, lactose, corn starch, and crystalline cellulose, and (ii) any one or both of carmellose calcium and sodium carboxymethyl starch.

[2] The pharmaceutical solid composition according to [1], wherein the component (i) is D-mannitol.

[3] The pharmaceutical solid composition according to [1] or [2], wherein the component (ii) is carmellose calcium.

[4] The pharmaceutical solid composition according to any one of [1] to [3], further comprising magnesium stearate or sodium stearyl fumarate.

[5] The pharmaceutical solid composition according to any one of [1] to [3], further comprising magnesium stearate.

[6] The pharmaceutical solid composition according to any one of [1] to [5], wherein the content of the compound represented by the formula (I) (in terms of its free form) is 0.5 to 25% by weight with respect to the total weight.

[7] The pharmaceutical solid composition according to any one of [1] to [5], wherein the content of the compound represented by the formula (I) (in terms of its free form) is 0.5 to 5% by weight with respect to the total weight.

[8] The pharmaceutical solid composition according to any one of [1] to [7], wherein the D-mannitol is D-mannitol having an average particle size smaller than 150 μm.

[9] The pharmaceutical solid composition according to any one of [1] to [7], wherein the D-mannitol is D-mannitol having an average particle size of 100 μm or smaller.

[10] The pharmaceutical solid composition according to any one of [1] to [9], wherein the content of the carmellose calcium is 2 to 20% by weight with respect to the total weight.

[11] The pharmaceutical solid composition according to any one of [1] to [9], wherein the content of the carmellose calcium is 5 to 15% by weight with respect to the total weight.

[12] The pharmaceutical solid composition according to any one of [4] to [11], wherein the content of magnesium stearate is 0.5 to 5% by weight with respect to the total weight.

[13] The pharmaceutical solid composition according to any one of [4] to [11], wherein the content of magnesium stearate is 1 to 3% by weight with respect to the total weight.

[14] The pharmaceutical solid composition according to any one of [1] to [13], wherein the pharmaceutical solid composition is a tablet.

[15] The pharmaceutical solid composition according to [14], wherein the tablet has a hardness of 20 N or higher, a friability of 20 or lower, and a disintegration time of 10 minutes or shorter.

[16] The pharmaceutical solid composition according to [14] or [15], wherein the tablet is prepared by mixing the compound represented by the formula (I) with D-mannitol and carmellose calcium and subsequently with magnesium stearate, followed by a direct compression method.

[17] A method for stabilizing a compound represented by the following formula (I), comprising allowing the compound represented by the formula (I) to coexist with D-mannitol, carmellose calcium, and magnesium stearate by mixing:

[Formula 4]

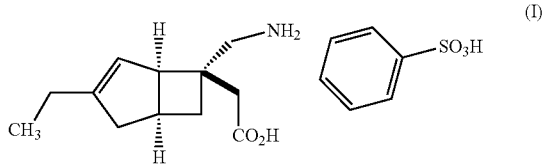

(I)

[18] The method according to [17], wherein the amount of a related substance produced after the mixture is left under conditions involving 40° C., 75% RH, and 6 months (in the presence of a desiccant) is 3% or lower.

Advantageous Effects of Invention

The present invention has overcome various difficulties in obtaining a stabilized pharmaceutical solid composition of compound (I). A feature of the present invention is that a stabilized pharmaceutical solid composition could be obtained at last.

The present invention has enabled the preparation of a stabilized pharmaceutical solid composition of compound (I) and further achieved solid preparations in the form of stabilized tablets, powders, granules, and capsules of compound (I) and the production of these solid preparations in the form of stabilized tablets, powders, granules, and capsules.

BRIEF DESCRIPTION OF DRAWINGS

FIG. 1 is a diagram showing the respective contents (%) of compound (I), carmellose calcium, and magnesium stearate in the abscissa and showing the total amount (%) of related substances of produced tablets under storage conditions involving 40° C., 75% RH, and 6 months in the ordinate.

FIG. 2 is a diagram showing the respective contents (%) of compound (I), carmellose calcium, and magnesium stearate in the abscissa and showing the hardness (N) of produced tablets in the ordinate.

DESCRIPTION OF EMBODIMENTS

Components and their Preferred Contents

Figure 3:
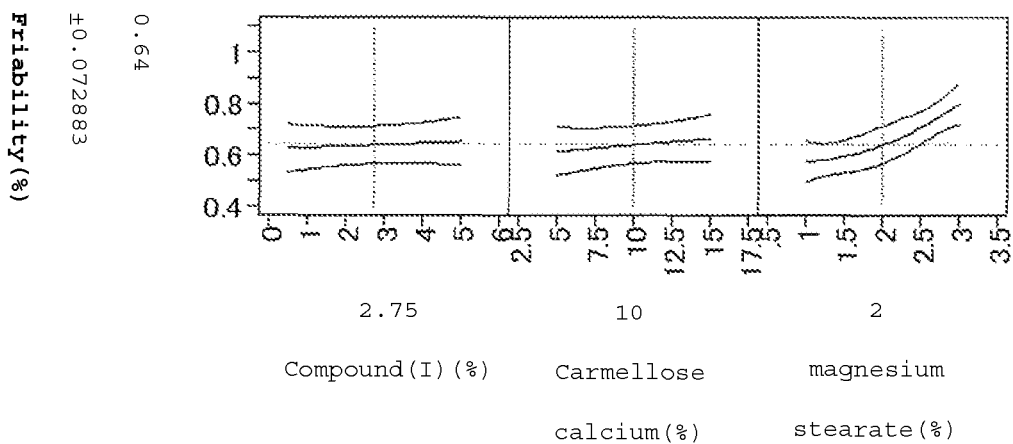
FIG. 3 is a diagram showing the respective contents (%) of compound (I), carmellose calcium, and magnesium stearate in the abscissa and showing the friability (%) of produced tablets in the ordinate.

The compound (I) used as an active ingredient in the present invention has individual particle sizes of preferably 60 μm (more preferably 40 μm) or smaller in terms of d50 particle size.

The content of compound (I) (in terms of its free form) used in the present invention is preferably 0.5 to 40% by weight, more preferably 0.5 to 25% by weight, particularly preferably 0.5 to 10% by weight (more particularly preferably 0.5 to 5% by weight), with respect to the total weight.

The content of excipient (preferably D-mannitol) used in the present invention is preferably 50 to 90% by weight, more preferably 60 to 90% by weight.

The average particle size of D-mannitol used in the present invention is desirably smaller than 150 μm, preferably 120 μm or smaller, more preferably 100 μm or smaller, particularly preferably 80 μm or smaller.

The content of disintegrant (preferably carmellose calcium, etc.) used in the present invention is preferably 2 to 20% by weight, more preferably 5 to 15% by weight, with respect to the total weight.

The content of binder (preferably hypromellose, etc.) used in the present invention is preferably 5 to 20% by weight, with respect to the total weight.

The content of lubricant (preferably magnesium stearate, sodium stearyl fumarate, etc., particularly preferably magnesium stearate) used in the present invention is preferably 0.5 to 5% by weight, more preferably 1 to 3% by weight, with respect to the total weight.

In the tablet according to the present invention, the preferred content of each component with respect to the total weight of its uncoated tablet is as follows:

Compound (I) (in terms of its free form): 0.5 to 25% by weight

Excipient (preferably D-mannitol): 50 to 90% by weight (average particle size: smaller than 150 μm)

Disintegrant (preferably carmellose calcium): 2 to 20% by weight

Lubricant (preferably magnesium stearate): 0.5 to 5% by weight

The content of each component is more preferably as follows:

Compound (I) (in terms of its free form): 0.5 to 10% by weight

Excipient (D-mannitol): 60 to 90% by weight (average particle size: 100 μm or smaller)

Disintegrant (carmellose calcium): 5 to 15% by weight

Lubricant (magnesium stearate): 1 to 3% by weight

Desirably, the tablet of the present invention has a hardness of 20 or 25 N or higher (more preferably 30 N or higher), a friability of 2% or lower (more preferably 1% or lower), and a disintegration time of 10 minutes or shorter.

(Method for Producing Solid Preparation)

The solid preparation of the present invention is obtained in the form of powders, granules, surface-coated granules, capsules, tablets, or surface-coated tablets by sequentially subjecting a powder of compound (I) serving as an active ingredient to:

(1) the addition of stabilizers such as an excipient and a disintegrant, and the further addition of auxiliaries necessary for formulation (a lubricant, etc.); and (2) an encapsulation step of compressing and encapsulating the resulting granular powder using a capsule-filling machine, or a tableting step of compressing the resulting granular powder using a tableting machine, and an optional coating step of coating the surface of the resulting granular powder, granules, or tablets.

Examples of the method for producing the solid preparation include: (1) a direct compression method which involves mixing the active ingredient with additives and directly compression-molding the mixture using a tableting machine; (2) a semi-direct compression method which involves granulating additives, mixing the granules with the active ingredient, and compression-molding the mixture; (3) a dry granule compression method which involves granulating the active ingredient and additives by a dry process, then adding a lubricant, etc. to the granules, and compression-molding the mixture; and (4) a wet granule compression method which involves granulating the active ingredient and additives by a wet process, then adding a lubricant, etc. to the granules, and compression-molding the mixture. An approach such as fluidized-bed granulation, high-speed mixer granulation, or melt granulation can be used as a granulation method. In the present invention, a method which involves preparing a tablet by directly compressing a mixed powder of the active ingredient without granulating a powder of the active ingredient is preferred.

For example, the method for producing a tablet according to the present invention is performed as described below.

The compound (I) serving as an active ingredient is pulverized. The particle size of the resulting powder is adjusted. Then, an excipient and/or a disintegrant are added to the powder, followed by mixing. Then, the mixture is sifted through a particle size selector. Then, a lubricant is added thereto, followed by further mixing. Then, the mixture is compressed using a tableting machine to obtain tablets.

The obtained tablets are preferably prepared into coated tablets using a coating machine.

Hereinafter, the present invention will be described in more detail with reference to the Examples. However, it should be understood that the Examples below are provided merely for describing the present invention and are not intended to limit the present invention.

EXAMPLES (Example 1) Stability Test on Additive

Compound (I) and an additive (an excipient or a disintegrant) were weighed at a ratio of 9:1 into an agate mortar and mixed for 3 minutes. The mixture was forcedly sifted through a 40-mesh sieve and then mixed in an agate mortar again to prepare a sample, which was then stored in small portions in clear vials (Daiichi Glass Co., Ltd.) under predetermined conditions.

Also, compound (I) was stored alone in small portions in clear vials under the same conditions.

The amount of related substances in the mixed powder before and after storage was measured using HPLC (Agilent 1100 or Agilent 1200). The results are shown in Table 1.

TABLE 1

| Additive | Purpose of formulation | Total amount of related substances* (%) | |
|---|---|---|---|
| | | 40° C./75% RH Open, 4 weeks | 60° C. Closed, 4 weeks |
| Lactose (Lactochem (sifted), Borculo DOMO INGREDIENTS) | Excipient | 0.76 | 1.71 |
| D-Mannitol (D-Mannitol, Merck KGaA) | Excipient | 0.03 | 0.86 |
| Crystalline cellulose (Ceolus(R) PH-101, Asahi Kasei Chemicals Corp.) | Excipient | 1.02 | 2.82 |
| Corn starch (Corn starch, Nihon Shokuhin Kako Co., Ltd.) | Excipient | 0.37 | 1.26 |
| Low-substituted hydroxypropylcellulose (L-HPC (LH-21), Shin-Etsu Chemical Co., Ltd.) | Disintegrant | 0.49 | 2.39 |
| Carmellose calcium (ECG-505, Gotoku Chemical Co., Ltd.) | Disintegrant | 0 | 0 |
| Croscarmellose sodium (Ac-Di-Sol, FMC) | Disintegrant | 1.71 | 9.17 |
| Sodium carboxymethyl starch (Explotab, JRS PHARMA JP) | Disintegrant | 0.53 | 0.11 |
| Crospovidone (Polyplasdone XL, ISP) | Disintegrant | 6.92 | 17.47 |

*Related substances include lactone derivatives of compound (I), etc.

The results of this test demonstrated that: D-mannitol, lactose, corn starch, and crystalline cellulose are preferred as excipient (particularly, D-mannitol is preferred); carmellose calcium (carboxymethylcellulose calcium) and sodium carboxymethyl starch are preferred as disintegrant (particularly, carmellose calcium is preferred); and these additives exhibit excellent stability in a mixture with compound (I).

(Example 2) Particle Size of D-Mannitol and Stability of Preparation (1) Preparation of Tablet Given amounts of compound (I), D-mannitol, and carmellose calcium were mixed for 10 minutes at the number of revolutions of 39 rpm using a V-shaped mixer (2 L). A given amount of sodium stearyl fumarate was further added to a sifted powder of the mixture, followed by mixing for 10 minutes at the number of revolutions of 39 rpm using a V-shaped mixer (2 L).

A sifted powder thereof was molded at a compressive pressure of approximately 10 kN using a tableting machine (Vela, Kikusui Seisakusho Ltd.) to obtain tablets (oblong tablets, 14.0×6.5 mm) each having a tablet mass of 400 mg. The content of each component is as shown in Table 2.

TABLE 2

| Component contained | Composition (mg/tablet) | | |
|---|---|---|---|
| | Example 2-1 | Comparative Example 2-1 | Comparative Example 2-2 |
| Compound (I) | 17.56 | 17.56 | 17.56 |
| (in terms of free form) | (10.00) | (10.00) | (10.00) |
| D-Mannitol (Parteck M100 (Merck))* | 330.4 | — | — |
| D-Mannitol (Parteck M200 (Merck))* | — | 330.4 | — |
| D-Mannitol (Pearlitol 200SD(Roquette))* | — | — | 330.4 |
| Carmellose calcium (ECG-505) | 40 | 40 | 40 |
| Sodium stearyl fumarate (JRS Pharma) | 12 | 12 | 12 |
| Total | 400 | 400 | 400 |

*Average particle size

Parteck M100 (Merck): 70 μm (Particle size distribution: 100 μm smaller: 40-55%; 100-212 μm; 25-50%; 212 μm or larger: 10-20%)

Parteck M200 (Merck): 150 μm (Particle size distribution: 100 μm smaller: 20-30%; 100-212 μm: 40-60%; 212 μm or larger: 20-30%)

Pearlitol 200SD (Roquette): 200 μm (2) Evaluation Method and Results

The tablets of Example 2-1 and Comparative Examples 2-1 and 2-2 prepared in paragraph (1) were left in plastic bottles for 4 weeks under conditions involving 25° C./60% RH, 40° C./75% RH, and 60° C. (in the presence of a desiccant (synthetic zeolite, MS-stick, Shin-Etsu Kasei Kogyo Co., Ltd)). Then, the amount of related substances was measured by HPLC (Agilent 1100 or Agilent 1200).

The results are shown in Table 3. The tablets containing Parteck M100 (average particle size: 70 μm) as D-mannitol produced related substances in the smallest amount under all of the storage conditions.

Particularly, during the storage at 60° C., the tablets containing Parteck M100 were shown to produce related substances in an amount equal to or lower than half the amount of those produced by the tablets containing any other D-mannitol.

The hardnesses of the tablets of Example 2-1 and Comparative Examples 2-1 and 2-2 were measured using a measurement apparatus PTB 302 (Pharma Test). As a result, the tablets of Example 2-1 had a hardness of 45.2 N, whereas the tablets of Comparative Example 2-2 had a hardness of 22.7 N. Thus, the tablets of Example 2-1 were shown to sufficiently satisfy the hardness standard (30 N) in consideration of production aptitude on this scale.

TABLE 3

(Total amount of related substances produced)

| Condition | Example 2-1 | Comparative Example 2-1 | Comparative Example 2-2 |
|---|---|---|---|
| 25° C./60% RH | 1.65% | 1.74% | 1.85% |
| 40° C./75% RH | 1.65% | 1.86% | 1.94% |
| 60° C. | 3.04% | 6.27% | 7.99% |

In the same way as in Example 1, a fine mannitol powder (D-mannitol EMPROVE) (average particle size: 75 μm or smaller) and D-mannitol Parteck M200 (average particle size: 150 μm) were each mixed with compound (I) at a ratio of 9:1 (mannitol:compound (I)). The mixtures were left for 4 weeks at 40° C. and 75% RH with petri dishes opened or at 60° C. in vials. Then, the amount of related substances was measured by HPLC (Agilent 1100 or Agilent 1200). The results are shown in Table 4. Parteck M200 having a large particle size (average particle size: 150 μm) was confirmed to result in a large amount of related substances produced, and poor compatibility. By contrast, use of the fine mannitol powder having a small average particle size was confirmed to exhibit excellent formulation stability (Example 2-2).

TABLE 4

| | 40° C./75% RH Open, 4 weeks | 60° C. Closed, 4 weeks |
|---|---|---|
| Fine mannitol powder (D-mannitol EMPROVE) | 0 | 0.07 |
| Parteck M200 (average particle size: 150 μm) | 0.01 | 1.19 |

In this context, the related substances are lactam derivatives of compound (I).

(Example 3) Amounts of Carmellose Calcium and Magnesium Stearate Mixed (1) Preparation of Tablets of Examples 3-1 to 3-13

Compound (I), D-mannitol, and carmellose calcium were weighed at mixing ratios shown in Table 5 and mixed for 10 minutes at the number of revolutions of 34 rpm using a V-shaped mixer (5 L). The mixture was sifted at 2200 rpm using COMIL (QC-U-10, Φ1.143, QUADRO) to prepare a sifted powder. Subsequently, magnesium stearate was weighed at a mixing ratio shown in Table 5 and added to the sifted powder, followed by mixing for 10 minutes at the number of revolutions of 34 rpm using a V-shaped mixer (5 L). The mixture was molded at a compressive pressure of approximately 10 kN using a tableting machine (Virgo, Kikusui Seisakusho Ltd.) to obtain uncoated tablets (active ingredient (in terms of free form): 0.5-10%, oblong tablets, 10.6×5.6 mm) each having a tablet mass of 200 mg.

The tablets were film-coated using a coating apparatus (High Coater Labo 30, Freund Corp.) at a charge air temperature of 75° C., a spray rate of approximately 6.5 g/min, and an exhaust gas temperature of approximately 51° C. (endpoint).

TABLE 5

| Component contained | Example No., composition (mg/tablet, (%)) | | | | | | | | | | | | |
|---|---|---|---|---|---|---|---|---|---|---|---|---|---|
| | 3-1 | 3-2 | 3-3 | 3-4 | 3-5 | 3-6 | 3-7 | 3-8 | 3-9 | 3-10 | 3-11 | 3-12 | 3-13 |
| Compound (I) (in terms of free form) | 9.66 5.5 (2.8) | 1.76 1 (0.5) | 1.76 1 (0.5) | 1.76 1 (0.5) | 9.66 5.5 (2.8) | 1.76 1 (0.5) | 9.66 5.5 (2.8) | 17.6 10 (5) | 17.6 10 (5) | 9.66 5.5 (2.8) | 17.6 10 (5) | 9.66 5.5 (2.8) | 17.6 10 (5) |
| D-mannitol (Parteck M100) | 166.3 (83) | 164.2 (82) | 184.2 (92) | 176.2 (88) | 174.3 (87) | 172.2 (86) | 178.3 (89) | 168.4 (84) | 156.4 (78) | 158.3 (79) | 160.4 (80) | 154.3 (77) | 148.4 (74) |
| Carmellose calcium (ECG-505) | 20 (10) | 30 (15) | 10 (5) | 20 (10) | 10 (5) | 20 (10) | 10 (5) | 10 (5) | 20 (10) | 30 (15) | 20 (10) | 30 (15) | 30 (15) |
| Magnesium stearate | 4 (2) | 4 (2) | 4 (2) | 2 (1) | 6 (3) | 6 (3) | 2 (1) | 4 (2) | 6 (3) | 2 (1) | 2 (1) | 6 (3) | 4 (2) |
| Total | 200 (100) | 200 (100) | 200 (100) | 200 (100) | 200 (100) | 200 (100) | 200 (100) | 200 (100) | 200 (100) | 200 (100) | 200 (100) | 200 (100) | 200 (100) |

(2) Evaluation Method and Results

The tablets of Examples 3-1 to 3-13 were left in plastic bottles under conditions involving 40° C., 75% RH, and 6 months (in the presence of a desiccant (synthetic zeolite, MS-stick, Shin-Etsu Kasei Kogyo Co., Ltd)). Then, the amount of related substances was measured by HPLC (Agilent 1100 or Agilent 1200).

Also, the hardnesses and friabilities of the tablets were measured using a tablet hardness meter (PTB-302) and a tablet friability tester (SZ-03), respectively. A disintegration test was conducted in accordance with the disintegration test method specified by Japanese Pharmacopoeia 16th edition. Exploratory statistical analysis software JMP® was used in analysis.

All of the tablets of Examples 3-1 to 3-13 were shown to be able to secure the target standard (3% or lower) for the total amount of related substances produced. Stable preparations were confirmed to be obtained within the implemented ranges of the amounts of carmellose calcium and magnesium stearate mixed (Tables 6 and 7 and FIG. 1).

The hardnesses tended to decrease with increase in the contents of compound (I), carmellose calcium, and magnesium stearate, and were all shown to present no problem (target hardness: 30 N or higher) within the implemented ranges of the amounts of carmellose calcium and magnesium stearate mixed (Table 7 and FIG. 2). The friabilities tended to increase with increase in the amounts of compound (I), carmellose calcium, and magnesium stearate mixed, and were all shown to present no problem (target friability: 10 or lower) within the implemented ranges of the amounts of carmellose calcium and magnesium stearate mixed (Table 7 and FIG. 3).

Figure 4:
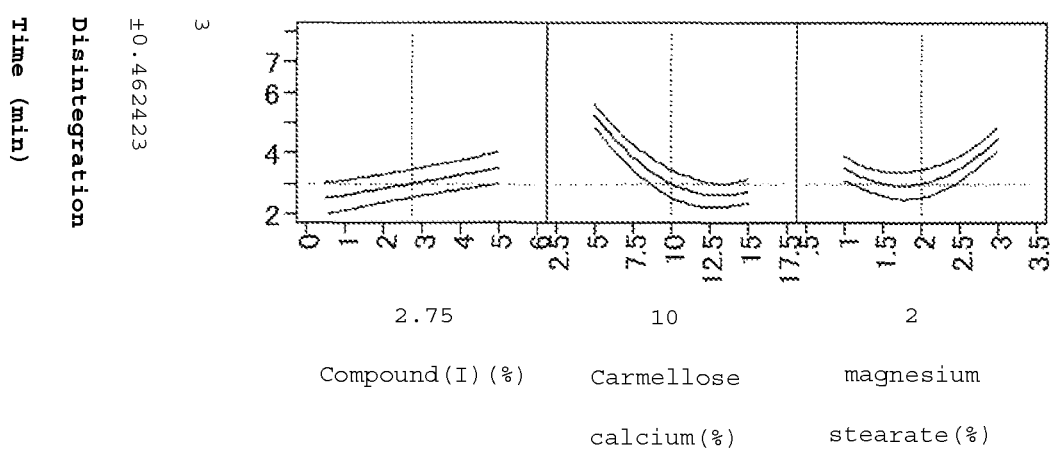
FIG. 4 is a diagram showing the respective contents (%) of compound (I), carmellose calcium, and magnesium stearate in the abscissa and showing the disintegration time (min) of produced tablets in the ordinate.

The disintegration times tended to increase with increase in the amounts of compound (I) and magnesium stearate mixed and with decrease in the amount of carmellose calcium mixed, and were shown to present no problem (target time: 10 minutes or shorter) within the implemented ranges of the amounts of carmellose calcium and magnesium stearate mixed (Table 7 and FIG. 4).

This demonstrated that tablets that are able to secure excellent stability and tablet physical properties can be prepared within the ranges of 0.5 to 5% of compound (I) (in terms of its free form), 5 to 15% (particularly, approximately 10%) of carmellose calcium, and 1 to 3% (particularly, approximately 2%) of magnesium stearate. Specifically, the tablets can achieve a total amount of related substances produced of 1.6% by weight or less, a hardness of 50 N or higher, a friability of 10 or lower, and a disintegration time of 6 minutes or shorter under conditions involving 40° C., 75% RH, and 6 months.

TABLE 6

(Total amount of related substances produced)

| Example No. | 3-1 | 3-2 | 3-3 | 3-4 | 3-5 | 3-6 | 3-7 | 3-8 | 3-9 | 3-10 | 3-11 | 3-12 | 3-13 |
|---|---|---|---|---|---|---|---|---|---|---|---|---|---|
| 40° C. 75% RH/ 6 months | 1.18 | 1.36 | 1.51 | 1.33 | 1.39 | 1.24 | 1.12 | 0.97 | 1.12 | 0.93 | 1.07 | 0.88 | 1.00 |

TABLE 7

| Example No. | 3-1 | 3-2 | 3-3 | 3-4 | 3-5 | 3-6 | 3-7 | 3-8 | 3-9 | 3-10 | 3-11 | 3-12 | 3-13 |
|---|---|---|---|---|---|---|---|---|---|---|---|---|---|
| Hardness (N) | 60 | 56 | 69 | 77 | 53 | 61 | 63 | 60 | 58 | 60 | 64 | 47 | 55 |
| Friability (%) | 0.6 | 0.7 | 0.6 | 0.6 | 0.7 | 0.7 | 0.6 | 0.7 | 0.8 | 0.5 | 0.6 | 1 | 0.6 |
| Disintegration time (min) | 3 | 3 | 4 | 3 | 7 | 4 | 6 | 6 | 5 | 3 | 4 | 4 | 3 |

(Example 4) Tablet Preparation Method and Stability (Example 4-1) Preparation of Tablet Compound (I), D-mannitol, carmellose calcium, and hypromellose were weighed as shown in Table 8 and mixed for 10 minutes at the number of revolutions of 39 rpm using a V-shaped mixer (500 mL). Then, the mixture was sifted through a sieve (60 mesh). Subsequently, sodium stearyl fumarate (JRS Pharma GmbH & Co. KG) was weighed and added to the sifted powder, followed by mixing for 10 minutes at the number of revolutions of 39 rpm using a V-shaped mixer (500 mL). The mixture was molded at a compressive pressure of approximately 10 kN using a tableting machine (Vela, Kikusui Seisakusho Ltd.) to obtain uncoated tablets (oblong tablets, 14.0×6.5 mm) each having a tablet weight of 400 mg.

The tablets were film-coated using a coating apparatus (High Coater Mini, Freund Corp.) at a charge air temperature of 95° C., a spray rate of approximately 2 g/min, and an exhaust gas temperature of approximately 40° C. (endpoint).

(Example 4-2) Preparation of Tablet

Compound (I), D-mannitol, and carmellose calcium were weighed as shown in Table 8 and mixed for 10 minutes at the number of revolutions of 32 rpm using a V-shaped mixer (10 L). Then, the mixture was sifted at 2200 rpm using COMIL (QC-197, Φ1.143, QUADRO) to prepare a sifted powder. Subsequently, magnesium stearate was weighed as shown in Table 8 and added to the sifted powder, followed by mixing for 10 minutes at the number of revolutions of 32 rpm using a V-shaped mixer (10 L). The mixture was molded at a compressive pressure of approximately 8 kN using a tableting machine (Vela, Kikusui Seisakusho Ltd.) to obtain uncoated tablets (oblong tablets, 6.0×11.5 mm) each having a tablet weight of 200 mg.

The tablets were film-coated using a coating apparatus (High Coater Labo 30, Freund Corp.) at a charge air temperature of 80° C., a spray rate of approximately 8 g/min, and an exhaust gas temperature of approximately 51° C. (endpoint).

(Example 4-3) Preparation of Tablet

Compound (I), D-mannitol, and carmellose calcium were weighed as shown in Table 8 and mixed for 10 minutes at the number of revolutions of 32 rpm using a V-shaped mixer (10 L). Then, the mixture was sifted at 2200 rpm using COMIL (QC-U-10, Φ1.143, QUADRO) to prepare a sifted powder. Subsequently, magnesium stearate was weighed as shown in Table 8 and added to the sifted powder, followed by mixing for 10 minutes at the number of revolutions of 32 rpm using a V-shaped mixer (10 L). The mixture was molded at a compressive pressure of approximately 8 kN using a tableting machine (Vela, Kikusui Seisakusho Ltd.) to obtain uncoated tablets (oblong tablets, 8.4×4.4 mm) each having a tablet weight of 100 mg.

The tablets were film-coated using a coating apparatus (High Coater Labo 30, Freund Corp.) at a charge air temperature of 75° C., a spray rate of approximately 5 g/min, and an exhaust gas temperature of approximately 55° C. (endpoint).

(Comparative Example 4-1) Preparation of Tablet

Compound (I), D-mannitol, and carmellose calcium were weighed as shown in Table 8 and granulated by spraying hypromellose 2910 suspended in water using a fluidized-bed granulation apparatus (Flow Coater Mini, Freund Corp.).

The amount of the suspension sprayed was set to an amount by which hypromellose 2910 was added at a mixing ratio shown in Table 8.

The granulated powder was sifted through a sieve (18 mesh). Subsequently, sodium stearyl fumarate was weighed as shown in Table 8 and added to the sifted powder, followed by mixing for 10 minutes at the number of revolutions of 45 rpm using a V-shaped mixer (1 L).

The mixture was molded at a compressive pressure of 10 kN using a tableting machine (Vela, Kikusui Seisakusho Ltd.) to obtain uncoated tablets (oblong tablets, 14.0×6.5 mm) each having a tablet mass of 400 mg.

The tablets were film-coated using a coating apparatus (High Coater Mini, Freund Corp.) at a charge air temperature of 95° C., a spray rate of approximately 2 g/min, and an exhaust gas temperature of approximately 40° C. (endpoint).

(Comparative Example 4-2) Preparation of Tablet

Compound (I), D-mannitol, and carmellose calcium were weighed as shown in Table 8 and granulated by adding dropwise hypromellose 2910 suspended in water using a high-speed mixer granulation apparatus (High-Speed Mixer LFS-GS-1J, Fukae Powtec Corp.).

The granulated powder was sifted through a sieve (8 mesh), then dried until an exhaust gas temperature of 50° C. using a fluidized-bed granulation apparatus (Flow Coater Mini, Freund Corp.), and then sifted through a sieve (12 mesh).

Sodium stearyl fumarate was weighed as shown in Table 8 and added to the sifted powder, followed by mixing for 10 minutes at the number of revolutions of 39 rpm using a V-shaped mixer (500 mL).

The mixture was molded at a compressive pressure of approximately 10 kN using a tableting machine (Vela, Kikusui Seisakusho Ltd.) to obtain uncoated tablets (oblong tablets, 14.0×6.5 mm) each having a tablet mass of 400 mg.

The tablets were film-coated using a coating apparatus (High Coater Mini, Freund Corp.) at a charge air temperature of 95° C., a spray rate of approximately 2 g/min, and an exhaust gas temperature of approximately 40° C. (endpoint).

TABLE 8

| | Composition (mg/tablet, (%)) | | | | |
| --- | --- | --- | --- | --- | --- |
| Component contained | Example 4-1 | Example 4-2 | Example 4-3 | Comparative Example 4-1 | Comparative Example 4-2 |
| Compound (I) | 17.56 | 17.56 | 0.878 | 17.56 | 17.56 |
| (in terms of free form) | 10 | 10 | 0.5 | 10 | 10 |
| | (2.5) | (5) | (0.5) | (2.5) | (2.5) |

TABLE 8-continued

| Component contained | Composition (mg/tablet, (%)) | | | | |
|---|---|---|---|---|---|
| | Example 4-1 | Example 4-2 | Example 4-3 | Comparative Example 4-1 | Comparative Example 4-2 |
| D-Mannitol (Parteck M100) | 318.4 | 158.44 | 87.122 | 318.4 | 318.4 |
| Carmellose calcium (ECG-505) | 40 (10) | 20 (10) | 10 (10) | 40 (10) | 40 (10) |
| Hypromellose 2910 (TC-5, Shin-Etsu Chemical Co., Ltd.) | 12 (3) | — | — | 12 (3) | 12 (3) |
| Sodium stearyl fumarate (JRS Pharma) | 12 (3) | — | — | 12 (3) | 12 (3) |
| Magnesium stearate (Coating agent) | — | 4 (2) | 2 (2) | — | — |
| Polyvinyl alcohol (Gohsenol EG-05P, The Nippon Synthetic Chemical Industry Co., Ltd.) | 8 | — | — | 8 | 8 |
| Titanium oxide (A-HR, Freund Corp.) | 5 | — | — | 5 | 5 |
| Polyethylene glycol (Macrogol 4000 (Sanyo Chemical Industries, Ltd.) | 4.04 | — | — | 4.04 | 4.04 |
| Talc (Matsumura Sangyo Co., Ltd.) | 2.96 | — | — | 2.96 | 2.96 |
| OPADRY-OY-S-9607 (Hypromellose) (Titanium oxide) (Talc) | — | 10 7.2 1.4 1.4 | 5 3.6 0.7 0.7 | — | — |
| Total | 420 | 210 | 105 | 420 | 420 |

(2) Evaluation Method

The tablets of Examples 4-1, 4-2, and 4-3 and Comparative Examples 4-1 and 4-2 were left in plastic bottles under conditions involving 25° C./60% RH/6 months, 40° C./75% RH/2 months, 40° C./75% RH/3 months, and 60° C./4 weeks (in the presence of a desiccant (synthetic zeolite, MS-stick, Shin-Etsu Kasei Kogyo Co., Ltd.)). Then, the amount of related substances was measured by HPLC (Agilent 1100 or Agilent 1200).

TABLE 9

(Amount of increase from initial total amount of related substances)

| Condition | Example 4-1 | Example 4-2 | Example 4-3 | Comparative Example 4-1 | Comparative Example 4-2 |
|---|---|---|---|---|---|
| 25° C./60% RH/6 months | 0% | 0.08% | — | 0.97% | 1.70% |
| 40° C./75% RH/2 months | 0.73% | — | 0.08% | 2.42% | 2.69% |
| 40° C./75% RH/3 months | — | 0.29% | 0.17% | — | — |
| 60° C./4 weeks | 4.50% | — | — | 11.08% | 16.52% |

The results demonstrated that under all of the storage conditions, the amount of related substances after storage was larger in Comparative Examples 4-1 and 4-2 than in Examples 4-1, 4-2, and 4-3. Specifically, the method for preparing tablets by the direct compression method was shown to be the best tablet preparation method, excellent in stability.

The invention claimed is:

1. A pharmaceutical composition comprising:
[(1R,5S,6S)-6-(aminomethyl)-3-ethylbicyclo[3.2.0]hept-3-en-6-yl]acetic acid monobenzenesulfonate of formula (I):

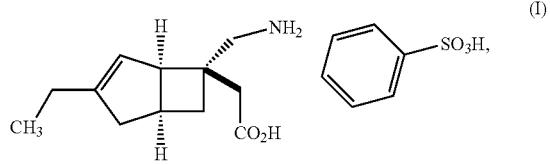

wherein the free form of the compound is present at 0.5 to 5% by weight of the total weight of the composition;
D-mannitol having an average particle size of 100 μm or smaller;
carmellose calcium at 5 to 15% by weight of the total weight of the composition; and
magnesium stearate at 1 to 3% by weight of the total weight of the composition.

2. The pharmaceutical composition of claim 1, wherein the pharmaceutical composition is a tablet.

3. The pharmaceutical composition of claim 2, wherein the tablet has a hardness of 20 N or higher, a friability of 2% or lower, and a disintegration time of 10 minutes or shorter.

4. A method of making the pharmaceutical composition of claim 2, comprising mixing the compound of formula (I) with D-mannitol and carmellose calcium and subsequently with magnesium stearate, and directly compressing the resulting mixture.

* * * * *